(12) United States Patent
Nishita et al.

(10) Patent No.: US 9,394,231 B2
(45) Date of Patent: Jul. 19, 2016

(54) COMPOSITION FOR FORMING ANTISTATIC FILM AND OLIGOMER COMPOUND

(71) Applicant: NISSAN CHEMICAL INDUSTRIES, LTD., Tokyo (JP)

(72) Inventors: Tokio Nishita, Toyama (JP); Ryuta Mizuochi, Toyama (JP); Rikimaru Sakamoto, Toyama (JP); Tomohisa Yamada, Funabashi (JP); Naoki Nakaie, Funabashi (JP); Yuki Takayama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 117 days.

(21) Appl. No.: 14/362,851

(22) PCT Filed: Nov. 12, 2012

(86) PCT No.: PCT/JP2012/079237
§ 371 (c)(1),
(2) Date: Jun. 4, 2014

(87) PCT Pub. No.: WO2013/084664
PCT Pub. Date: Jun. 13, 2013

(65) Prior Publication Data
US 2015/0008372 A1 Jan. 8, 2015

(30) Foreign Application Priority Data

Dec. 5, 2011 (JP) .................................. 2011-265880
Jun. 29, 2012 (JP) .................................. 2012-147614

(51) Int. Cl.
*H01B 1/00* (2006.01)
*C07C 211/54* (2006.01)
(Continued)

(52) U.S. Cl.
CPC .......... *C07C 211/54* (2013.01); *C08G 73/0266* (2013.01); *C08L 79/02* (2013.01); *C09D 179/02* (2013.01); *G03F 7/093* (2013.01);
(Continued)

(58) Field of Classification Search
CPC .............. H01B 1/00; H01B 1/28; C09K 3/16; C07C 209/10; C07C 211/54; G03F 7/11; C07B 61/00
See application file for complete search history.

(56) References Cited

U.S. PATENT DOCUMENTS 6,153,726 A    11/2000  Kathirgamanathan et al.
7,455,792 B2 *  11/2008  Yoshimoto ......... C08G 73/0266
                                                      252/500

(Continued)

FOREIGN PATENT DOCUMENTS

CN    101088992 A    12/2007
JP    A-08-201979    8/1996
(Continued)

OTHER PUBLICATIONS

International Search Report issued in International Patent Application No. PCT/JP2012/079237 mailed on Feb. 5, 2013.
(Continued)

*Primary Examiner* — Mark Kopec
(74) *Attorney, Agent, or Firm* — Oliff PLC

(57) ABSTRACT

A composition for forming an antistatic film, includes: an oligomer compound of Formula (1A):

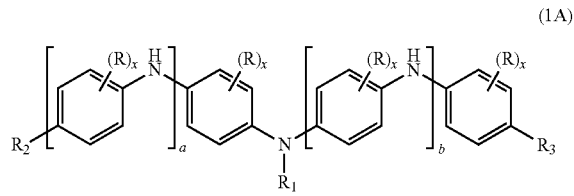

(where $R_1$ is a hydrogen atom or a group of Formula (2), each of $R_2$ and $R_3$ is independently a hydrogen atom, a group of Formula (3), or a group of Formula (4), at least one of the plurality of Rs is a sulfo group, a and b are positive integers satisfying $2 \leq (a+b) \leq 6$; and each of a plurality of xs is independently an integer from 0 to 4):

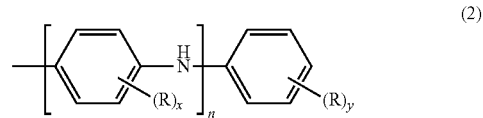

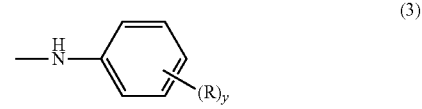

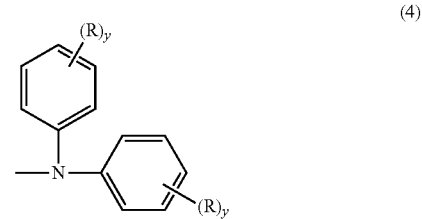

(where n is an integer satisfying $1 \leq n < (a+b+4)$; a, b, a plurality of Rs, and x are the same as those in Formula (1A); and each of a plurality of ys is independently an integer from 0 to 5); and water.

8 Claims, No Drawings

(51) Int. Cl.
  *G03F 7/09*   (2006.01)
  *H01B 1/12*   (2006.01)
  *C09D 179/02*  (2006.01)
  *C08L 79/02*   (2006.01)
  *C08G 73/02*   (2006.01)
  *G03F 7/11*   (2006.01)
  *G03F 1/00*   (2012.01)

(52) U.S. Cl.
  CPC ............... *H01B 1/128* (2013.01); *G03F 1/00* (2013.01); *G03F 7/11* (2013.01)

(56) References Cited

U.S. PATENT DOCUMENTS 8,298,444 B2 * 10/2012 Yamada ............... C07C 211/54 252/500

2006/0232198 A1 * 10/2006 Kawamura ............ C07C 211/54 313/504
2010/0230639 A1    9/2010 Yamada et al.

FOREIGN PATENT DOCUMENTS

| JP | A-11-279279 | 10/1999 |
|---|---|---|
| JP | A-2000-044683 | 2/2000 |
| JP | A-2006-301073 | 11/2006 |
| JP | A-2010-020046 | 1/2010 |
| WO | WO 2008/129947 A1 | 10/2008 |
| WO | WO 2010/058777 A1 | 5/2010 |

OTHER PUBLICATIONS

Written Opinion of the International Searching Authority issued in International Patent Application No. PCT/JP2012/079237 mailed on Feb. 5, 2013.

* cited by examiner

COMPOSITION FOR FORMING ANTISTATIC FILM AND OLIGOMER COMPOUND

TECHNICAL FIELD

The present invention relates to a composition for forming an antistatic film that is formed, for example, on a resist film. The present invention also relates to an oligomer compound used for the composition.

BACKGROUND ART

Electron beams have been used for preparing photomasks or reticles that are used in photolithographic process. Further, a lithography technique employing an electron beam is one of candidates of advanced fine processing techniques of the next generation. Electron beam lithography has advantages compared to conventional photolithography utilizing an excimer laser in that fine patterns can be formed, effects of a standing wave generated from a substrate located under a resist film are not observed and the like.

However, there is a problem that, when a resist film is irradiated with an electron beam in electron beam lithography, an electron is easily charged up onto the surface of the resist film.

To solve this problem, Patent Document 1 discloses a composition for forming an antistatic film on the top layer of an electron beam resist. The composition contains an ionic liquid showing ionic conductivity and a water-soluble resin to prevent static charge. In addition, Patent Document 2 discloses a conductive composition for forming a fine resist pattern with a charged particle beam such as an electron beam, an ion beam and the like. The conductive composition contains an aniline conductive polymer being substituted with an acidic group.

PRIOR ART DOCUMENTS

Patent Documents

Patent Document 1: Japanese Patent Application Publication No. 2010-020046 (JP 2010-020046 A)
Patent Document 2: Japanese Patent Application Publication No. 2006-301073 (JP 2006-301073 A)

SUMMARY OF THE INVENTION

Problem to be Solved by the Invention

Since the conductive composition disclosed in Patent Document 2 contains a conductive polymer, an antistatic film can be formed on a resist film with the conductive composition. However, in case that the molecular weight of the conductive polymer contained is large, the conductive polymer is unlikely to be dissolved but is dispersed in a solvent, and thus when it coated onto a resist film, the surface becomes uneven. In contrast, as to an antistatic film obtained from a composition containing an ionic liquid, an ion in the film serves to release electric charge of an electron beam. However, since the number of the ion is limited, it is gradually charged up in drawing with the beam.

It is an object of the present invention to obtain a composition for forming an antistatic film that has a superior coating performance onto the surface of a resist film and forms antistatic film capable of protecting a resist film from being charged by a charged particle beam.

Also, it is an object of the present invention to provide an oligomer compound containing a sulfo group suitably used for the composition for forming the antistatic film of above, and an oligomer compound that is a precursor of the oligomer compound.

Further, it is an object of the present invention to provide a method for efficiently manufacturing the precursor oligomer compound.

Means for Solving the Problem

The present invention is a composition for forming an antistatic film, comprising:
an oligomer compound of Formula (1A):

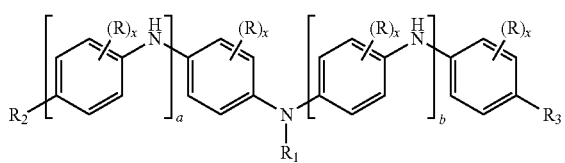

(where $R_1$ is a hydrogen atom or a group of Formula (2); each of $R_2$ and $R_3$ is independently a hydrogen atom, a group of Formula (3), or a group of Formula (4); each of a plurality of Rs is independently a halogen atom, a hydroxy group, an amino group, a silanol group, a thiol group, a carboxy group, a carbamoyl group, a phosphoric acid group, a phosphoester group, an ester group, a thioester group, an amido group, a nitro group, a $C_{1-20}$ primary hydrocarbon group, secondary hydrocarbon group, or tertiary hydrocarbon group, a $C_{1-20}$ organoxy group, a $C_{1-20}$ organoamino group, a $C_{1-20}$ organosilyl group, a $C_{1-20}$ organothio group, an acyl group, or a sulfo group, and at least one of the plurality of Rs is a sulfo group; a and b are positive integers satisfying 2≤(a+b)≤6; and each of a plurality of xs is independently an integer from 0 to 4):

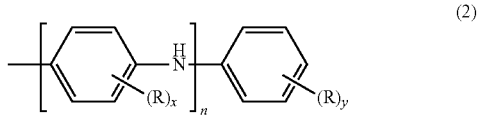

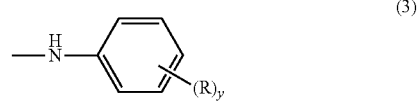

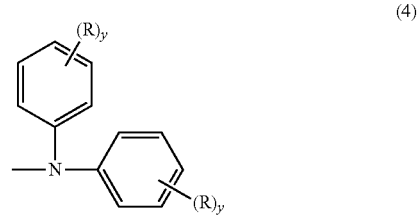

(where n is an integer satisfying 1≤n<(a+b+4); a, b, a plurality of Rs, and x are the same as those in Formula (1A); and each of a plurality of ys is independently an integer from 0 to 5); and water.

The present invention also includes an oligomer compound of Formula (1A):

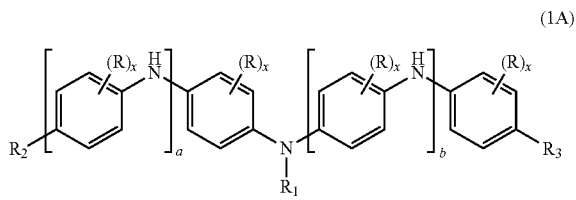

(1A)

(where $R_1$ is a hydrogen atom or a group of Formula (2); each of $R_2$ and $R_3$ is independently a hydrogen atom, a group of Formula (3), or a group of Formula (4); each of a plurality of Rs is independently a halogen atom, a hydroxy group, an amino group, a silanol group, a thiol group, a carboxy group, a carbamoyl group, a phosphoric acid group, a phosphoester group, an ester group, a thioester group, an amido group, a nitro group, a $C_{1-20}$ primary hydrocarbon group, secondary hydrocarbon group, or tertiary hydrocarbon group, a $C_{1-20}$ organoxy group, a $C_{1-20}$ organoamino group, a $C_{1-20}$ organosilyl group, a $C_{1-20}$ organothio group, an acyl group, or a sulfo group, and at least one of the plurality of Rs is a sulfo group; a and b are positive integers satisfying $2 \leq (a+b) \leq 6$; and each of a plurality of xs is independently an integer from 0 to 4):

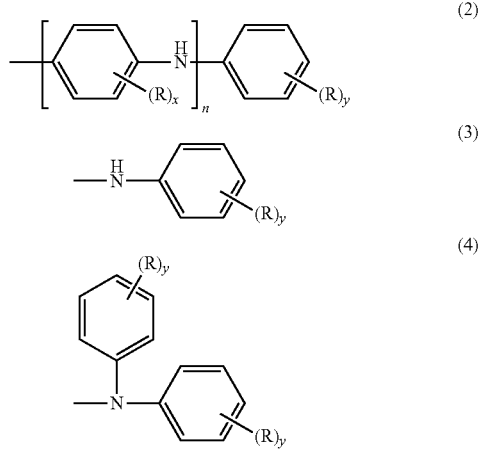

(2)

(3)

(4)

(where n is an integer satisfying $1 \leq n < (a+b+4)$; a, b, a plurality of Rs, and x are the same as those in Formula (1A); and each of a plurality of ys is independently an integer from 0 to 5).

The present invention further relates to an oligomer compound of Formula (1C) that is a precursor of the compound of Formula (1A):

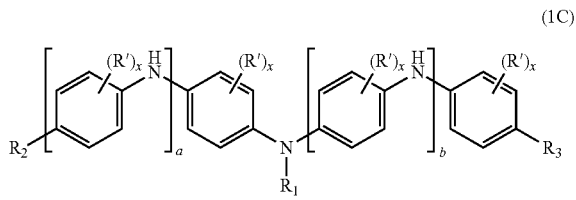

(1C)

(where $R_1$ is a hydrogen atom or a group of Formula (2'); each of $R_2$ and $R_3$ is independently a hydrogen atom, a group of Formula (3'), or a group of Formula (4'); each of a plurality of R's is independently a halogen atom, a hydroxy group, an amino group, a silanol group, a thiol group, a carboxy group, a carbamoyl group, a phosphoric acid group, a phosphoester group, an ester group, a thioester group, an amido group, a nitro group, a $C_{1-20}$ primary hydrocarbon group, secondary hydrocarbon group, or tertiary hydrocarbon group, a $C_{1-20}$ organoxy group, a $C_{1-20}$ organoamino group, a $C_{1-20}$ organosilyl group, a $C_{1-20}$ organothio group, an acyl group, or a sulfo group; a and b are positive integers satisfying $2 \leq (a+b) \leq 6$; and each of a plurality of xs is independently an integer from 0 to 4):

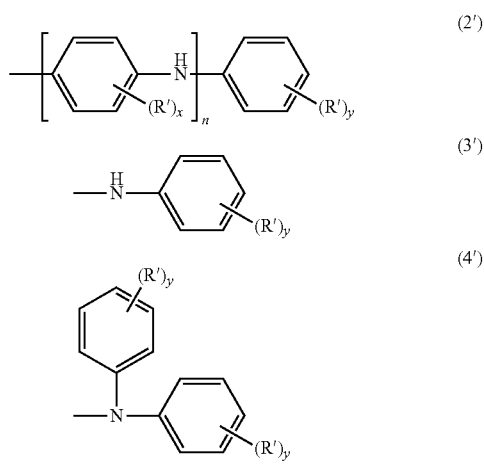

(2')

(3')

(4')

(where n is an integer satisfying $1 \leq n < (a+b+4)$; a, b, a plurality of R's, and x are the same as those in Formula (1C); and each of a plurality of ys is independently an integer from 0 to 5).

The present invention also relates to a method for manufacturing an aniline oligomer compound of Formula (1F) below, characterized by a coupling reaction applicable to a method for manufacturing an oligomer compound of Formula (1C), in which a triphenylamine derivative of Formula (1D) below is caused to react with an amine compound of Formula (1E) in the presence of a metal complex catalyst and a base:

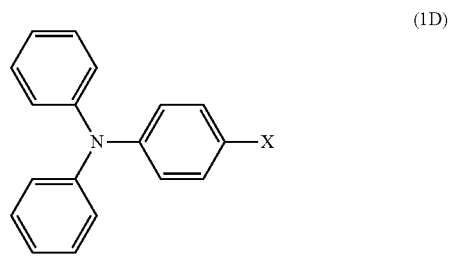

(1D)

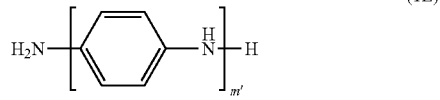

(1E)

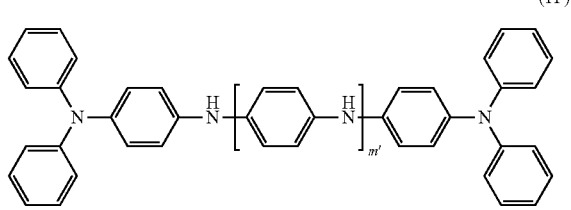

(1F)

(where X is a leaving functional group, and m' is an integer from 1 to 3).

Effects of the Invention

An antistatic film obtained from the composition for forming an antistatic film of the present invention prevents charge up induced by an electron beam and an environmental effect to a resist, and presence of the antistatic film allows a desired resist pattern to be formed. The antistatic film can be thus used for a wide range of applications, such as manufacturing a photomask that is used for manufacturing semiconductor elements and liquid crystal panels; and manufacturing LSIs by lithography utilizing an electron beam, and is industrially extremely beneficial. In addition, with a sulfonated water soluble resin contained in the composition for forming an antistatic film, a coating performance onto a resist film can be greatly improved. Furthermore, the composition for forming an antistatic film is prevented from being gradually charged during drawing with an electron beam due to the limited number of ions in the film.

Oligomer compounds that can be used for a variety of applications, such as an oligomer compound of Formula (1C) that is a precursor of an oligomer compound of Formula (1A) of the present invention, can be manufactured by a method for manufacturing an aniline oligomer of the present invention. In particular, the manufacturing method of the present invention does not require the use of reagents that are difficult to obtain as a commercial product, are not necessarily low in price and the like. In addition, the manufacturing method of the present invention does not require a plurality of steps, such as a step for introduction of a protecting group and a step for deprotection. Thus, oligomer compounds can be manufactured by the method with raw materials and reagents that are relatively low in price and readily available, and in a short process. Moreover, a reaction in the manufacturing method of the present invention proceeds efficiently, and thus a target compound can be manufactured by the method in a short time at a high yield.

MODES FOR CARRYING OUT THE INVENTION

<<Composition for Forming Antistatic Film>>
[Oligomer Compound]

A composition for forming an antistatic film of the present invention contains an oligomer compound of Formula (1A), and the oligomer compound of Formula (1A) can be obtained by sulfonating an aniline oligomer compound not having any sulfo groups.

The number of benzene rings contained in the main chain of the oligomer compound is preferably not more than 10, because the molecular weight of the oligomer compound is not too large. Thus, in Formula (1A), a and b are positive integers satisfying $2 \leq (a+b) \leq 6$. In addition, the number of benzene rings contained in Formula (2) should be less than the number of benzene rings contained in the main chain of the oligomer compound, and thus in Formula (2), n is an integer satisfying $1 \leq n < (a+b+4)$.

In Formula (1A), examples of a $C_{1-20}$ primary hydrocarbon group, secondary hydrocarbon group, and tertiary hydrocarbon group include methyl group, ethyl group, n-propyl group, isopropyl group, n-butyl group, sec-butyl group, isobutyl group, tert-butyl group, n-pentyl group, isopentyl group, n-hexyl group, n-octyl group, 2-ethylhexyl group, decyl group, cyclopentyl group, cyclohexyl group, bicyclohexyl group, 1-butenyl group, 2-butenyl group, 3-butenyl group, hexenyl group, vinyl group, 1-propenyl group, 2-propenyl group, isopropenyl group, 1-methyl-2-propenyl group, phenyl group, xylyl group, tolyl group, biphenyl group, naphthyl group, benzyl group, phenylethyl group, and phenylcyclohexyl group. Examples of a $C_{1-20}$ organoxy group include alkoxy groups, such as methoxy group, ethoxy group, n-propoxy group, isopropoxy group, n-butoxy group, sec-butoxy group, and tert-butoxy group; alkenyloxy groups, such as 1-butenyloxy group, 2-butenyloxy group, 3-butenyloxy group, hexenyloxy group, vinyloxy group, 1-propenyloxy group, 2-propenyloxy group, isopropenyloxy group, and 1-methyl-2-propenyloxy group; and aryloxy groups, such as phenyloxy group, xylyloxy group, tolyloxy group, biphenyloxy group, and naphthyloxy group. Examples of a $C_{1-20}$ organo amino group include methyl amino group, ethyl amino group, propyl amino group, butyl amino group, pentyl amino group, hexyl amino group, heptyl amino group, octyl amino group, nonyl amino group, decyl amino group, lauryl amino group, dimethyl amino group, diethyl amino group, dipropyl amino group, dibutyl amino group, dipentyl amino group, dihexyl amino group, diheptyl amino group, dioctyl amino group, dinonyl amino group, didecyl amino group, dicyclohexyl amino group, morpholino group, and biphenyl amino group. Examples of a $C_{1-20}$ organosilyl group include trimethylsilyl group, triethylsilyl group, tripropylsilyl group, tributylsilyl group, tripentylsilyl group, trihexylsilyl group, pentyldimethylsilyl group, hexyldimethylsilyl group, octyldimethylsilyl group, and decyldimethylsilyl group. Examples of a $C_{1-20}$ organothio group include methylthio group, ethylthio group, propylthio group, butylthio group, pentylthio group, hexylthio group, heptylthio group, octylthio group, nonylthio group, decylthio group, and laurylthio group. Examples of an acyl group include formyl group, acetyl group, propionyl group, butyryl group, isobutyryl group, valeryl group, isovaleryl group, hexanoyl group, octanoyl group, decanoyl group, lauroyl group, and benzoyl group. Examples of a halogen atom include fluorine atom, chlorine atom, bromine atom, and iodine atom.

Examples of a phosphoester group include a —P(=O)(OH)(OR$_4$) group and a —P(=O)(OR$_4$)(OR$_5$) group. Examples of an ester group include a —C(=O)OR$_4$ group and a —O—C(=O)R$_4$ group. Examples of a thioester group include a —C(=O)SR$_4$ group and a —S—C(=O)R$_4$ group. Examples of an amido group include a —C(=O)—NHR$_4$ group and a —C(=O)—NR$_4$R$_5$ group. Each of R$_4$ and R$_5$ is independently a hydrocarbon group. Examples thereof include a $C_{1-8}$ alkyl group, a cycloalkyl group, an alkenyl group, an aryl group, and an aralkyl group, such as methyl group, ethyl group, n-propyl group, isopropyl group, n-butyl group, sec-butyl group, isobutyl group, tert-butyl group, n-pentyl group, isopentyl group, n-hexyl group, n-octyl group, 2-ethylhexyl group, cyclopentyl group, cyclohexyl group, 1-butenyl group, 2-butenyl group, 3-butenyl group, hexenyl group, vinyl group, 1-propenyl group, 2-propenyl group, isopropenyl group, 1-methyl-2-propenyl group, phenyl group, xylyl group, tolyl group, benzyl group, and phenylethyl group.

The composition for forming an antistatic film of the present invention may further comprise an oligomer compound of Formula (1B) below, and the oligomer compound is an oxidized form generated as a by-product when obtaining an oligomer compound of Formula (1A) (where R$_1$ is a hydrogen atom) by sulfonation:

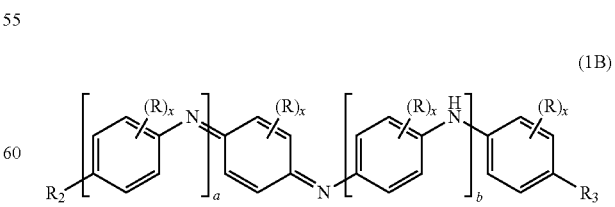

(1B)

(where R$_2$, R$_3$, a plurality of Rs, a, b, and a plurality of xs are the same as those in Formula (1A)).

The weight average molecular weight of the oligomer compound contained in the composition for forming an antistatic film of the present invention is, for example, 500 or larger and smaller than 5,000. When the value of the weight average molecular weight is too large, the oligomer compound is not dissolved but is dispersed in water.

[Solvent]

The composition for forming an antistatic film of the present invention contains water as a solvent. If necessary, the composition may further contain as a solvent a polar organic solvent, in addition to water. An organic solvent used in the present invention is not particularly limited as long as the oligomer compound of above can be dissolved therein, and the organic solvent can be dissolved in water. Examples of the organic solvent include alcohols, such as methanol, ethanol, isopropyl alcohol, propyl alcohol, and butanol; ketones, such as acetone and ethyl isobutyl ketone; ethylene glycols, such as ethyl lactate, ethylene glycol, and ethylene glycol methyl ether; propylene glycols, such as propylene glycol, propylene glycol methyl ether, propylene glycol ethyl ether, propylene glycol butyl ether, and propylene glycol propyl ether; amides, such as dimethylformamide and dimethylacetamide; and pyrrolidones, such as N-methyl-2-pyrrolidone and N-ethyl pyrrolidone. Among them, alcohols and ethylene glycols are preferably used. These organic solvents are used alone, or two or more of them are used in combination.

Among the polar organic solvents of above, ethylene glycol monomethyl ether is more preferable. When a composition for forming an antistatic film of the present invention contains the organic solvent of above, the amount thereof is, for example, from 5 wt % to 40 wt %, for the amount of 100 wt % of water.

The ratio of the solid content, which is a content of the composition for forming an antistatic film of the present invention excluding the solvent, is, for example, from 0.1 wt % to 15.0 wt % and preferably from 1.0 wt % to 5.0 wt %, with respect to 100 wt % of the composition.

[Surfactant]

If necessary, the composition for forming an antistatic film of the present invention may further comprise a surfactant, as long as the effect of the present invention is not impaired. The surfactant is an additive to improve a coating performance of the composition onto a substrate. Known surfactants, such as nonionic surfactants and fluorine surfactants, can be used.

Specific examples of the surfactant include nonionic surfactants including polyoxyethylene alkylethers, such as polyoxyethylene lauryl ether, polyoxyethylene stearyl ether, polyoxyethylene cetyl ether, and polyoxyethylene oleyl ether; polyoxyethylene alkylarylethers, such as polyoxyethylene octyl phenyl ether and polyoxyethylene nonyl phenyl ether; polyoxyethylene-polyoxypropylene block copolymers; sorbitan fatty acid esters, such as sorbitan monolaurate, sorbitan monopalmitate, sorbitan monostearate, sorbitan monooleate, sorbitan trioleate, and sorbitan tristearate; and polyoxyethylene sorbitan fatty acid esters, such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine surfactants including Eftop [registered trademark] EF301, EF303, and EF352 (manufactured by Mitsubishi Materials Electronic Chemicals Co., Ltd.), MEGAFAC [registered trademark] F171, F173, and R30 (manufactured by DIC Corporation), Fluorad FC430 and FC431 (manufactured by Sumitomo 3M Limited), and AsahiGuard [registered trademark] AG710, SURFLON [registered trademark] S-382, SC101, SC102, SC103, SC104, SC105, and SC106 (manufactured by Asahi Glass Co., Ltd.); organosiloxane polymer KP341 (manufactured by Shin-Etsu Chemical Co., Ltd.); and Olfine [registered trademark] EXP.4200 (manufactured by Nissin Chemical Industry Co., Ltd.). These surfactants may be added alone, or two or more of them may be added in combination.

When a composition for forming an antistatic film of the present invention contains the surfactant of above, the amount thereof is from 0.05 wt % to 1 wt %, and most suitably 0.1 wt %, with respect to 100 wt % of the solvent contained in the composition.

[Basic Compound]

If necessary, the composition for forming an antistatic film of the present invention may further comprise a basic compound, as long as the effect of the present invention is not impaired. By mixing the basic compound into a composition for forming an antistatic film of the present invention, the composition becomes neutral or weakly alkaline, whereby a chemical solution can be preferably easily processed, and corrosion of a device and a duct can be preferably reduced. Furthermore, by using these amines and ammonium salts as a mixture, conductivity can be improved.

By using a mixture of an amine and an ammonium salt, or a quaternary ammonium salt as the basic compound of above, conductivity can be improved. Examples of the mixture include $NH_3/(NH_4)_2CO_3$, $NH_3/(NH_4)HCO_3$, $NH_3/CH_3COONH_4$, $N(CH_3)_3/(NH_4)_2CO_3$, and $N(CH_3)_3/CH_3COONH_4$. The preferable mixing ratio of the mixture is an amine/an ammonium salt=1/10 to 10/1. Examples of the quaternary ammonium salt include $(CH_3)_4NOH$, $(CH_2CH_3)_4NOH$, and $(CH_2CH_2CH_3)_4NOH$. The basic compounds are not limited to a mixture of two types of compounds, and the compounds can be added alone, or two or more types of them can be added in combination.

When a composition for forming an antistatic film of the present invention contains the basic compound of above, the amount thereof is, for example, from 0.01% by mass to 30 wt % and preferably from 0.5 wt % to 20 wt %, with respect to 100 wt % of the solvent contained in the composition. If the amount of the basic compound is over 20 wt %, a solution becomes strongly basic, and conductivity is decreased. When a mixture of an amine and an ammonium salt is used as the basic compound of above, pH of a solution can be optionally adjusted by changing concentrations, types, and mixing ratios of amines and ammonium salts. The pH of the composition for forming an antistatic film of the present invention is adjusted within a range from 5 to 12 for use.

[Formation of Antistatic Film]

For use, a composition for forming an antistatic film of the present invention is applied onto a resist film formed on a substrate, and baked. Application of the composition is conducted, for example, by a spinner or a coater. After a coated film is obtained by the application, a step for drying the coated film is required. A temperature for drying is from 70.0° C. to 150.0° C. and preferably from 90.0° C. to 140.0° C. The step for drying can be conducted, for example, on a hot plate, by heating a substrate at a temperature from 50° C. to 100° C., for 0.1 minute to 10 minutes. Alternatively, the step for drying can be conducted, for example, by air-drying at room temperature (about 20° C.).

<<Oligomer Compound and Precursor Thereof>>

An oligomer compound of Formula (1A) can be obtained by sulfonating a compound of Formula (1C) below, which is a precursor of the oligomer compound of Formula (1A). Note that both of the oligomer compound of Formula (1A) and the oligomer compound of Formula (1C) are included in the present invention.

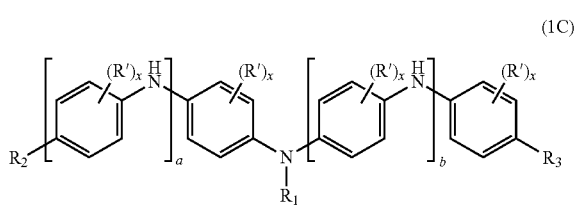

(1C)

(where $R_1$ is a hydrogen atom or a group of Formula (2'); each of $R_2$ and $R_3$ is independently a hydrogen atom, a group of Formula (3'), or a group of Formula (4'); each of a plurality of R's is independently a halogen atom, a hydroxy group, an amino group, a silanol group, a thiol group, a carboxy group, a carbamoyl group, a phosphoric acid group, a phosphoester group, an ester group, a thioester group, an amido group, a nitro group, a $C_{1-20}$ primary hydrocarbon group, secondary hydrocarbon group, or tertiary hydrocarbon group, a $C_{1-20}$ organoxy group, a $C_{1-20}$ organoamino group, a $C_{1-20}$ organosilyl group, a $C_{1-20}$ organothio group, an acyl group, or a sulfo group; a and b are positive integers satisfying $2 \leq (a+b) \leq 6$; and each of a plurality of xs is independently an integer from 0 to 4):

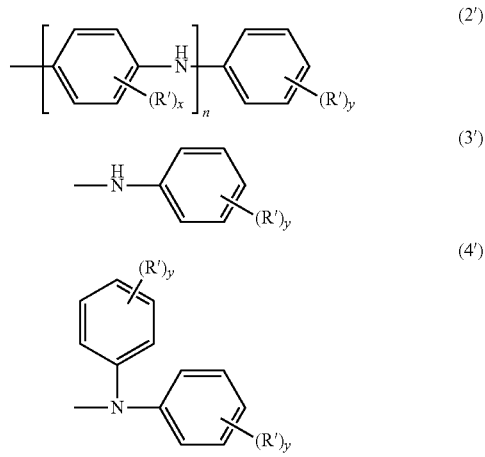

(2')

(3')

(4')

(where n is an integer satisfying $1 \leq n < (a+b+4)$; a, b, a plurality of R's, and x are the same as those in Formula (1C); and each of a plurality of ys is independently an integer from 0 to 5).

Specific examples of each of the groups in an oligomer compound of Formula (1C) are the same as those of each of the groups in an oligomer compound of Formula (1A).

An oligomer compound of Formula (1C) turns to an oligomer compound of Formula (1A) when the oligomer compound of Formula (1C) is sulfonated using a conventional sulfonating agent, such as chlorosulfonic acid, fuming sulfuric acid, 1,3,5-trimethylbenzene-2-sulfonic acid, 1,2,4,5-tetramethylbenzene-3-sulfonic acid, 1,2,3,4,5-pentamethylbenzene-6-sulfonic acid, sulfuric acid, and sulfur trioxide, in a protic solvent, for example, an organic solvent such as 1,2-dichloroethane, 1,1,2,2-tetrachloroethane, chloroform, carbon tetrachloride, and o-dichlorobenzene.

<<Method for Manufacturing Precursor (Oligomer Compound)>>

As described above, an aniline oligomer compound of Formula (1A) and an aniline polymer being substituted with an acidic group (a sulfonic acid group) disclosed in Patent Document 2 can be manufactured by sulfonating a precursor that is an aniline oligomer compound/aniline polymer not containing any acidic groups with a sulfonating agent or the like.

Here, the precursor that is the aniline polymer or the aniline oligomer compound is very useful as an important intermediate not only for conductive materials, but also in a wide range of fields, including medicines and agrichemicals. For example, the superior charge transporting property of aniline oligomer compounds having triphenylamine structures due to the structure has been attracting attention.

Among these aniline oligomer compounds, the aniline oligomer having a triphenylamine structure can be obtained from an aniline oligomer compound through a plurality of steps including (1) step for bromination, (2) step for protection of an amino group with a protecting group (tert-butoxycarbonyl group or the like), (3) step for coupling with diphenylamine, and (4) step for deprotection of the protecting group (WO 2008/129947).

However, the aforementioned conventional manufacturing method has disadvantages both in production efficiency and economic efficiency. That is, for example, that method requires a plurality of steps and thus requires many tasks and long time; if an aniline oligomer compound of a starting material is not commercially available, a step for preparing it is further required; and a brominating agent (for example, tetrabutyl ammonium tribromide) used in a step for bromination, a reagent (di-tert-butyl dicarbonate) used in a step for protection, and the like are not necessarily low in price, and they need to be used in amounts larger than equivalents considering the number of functional groups involved in the reaction.

The inventors of the present invention have studied a manufacturing method that can be conducted with fewer steps, at low prices using commercially available raw materials, and with a high yield. As a result, the inventors have found that some of the aforementioned precursors, for example, a compound of Formula (1C), in which $R_1$ is a hydrogen atom; each of $R_2$ and $R_3$ is a group of Formula (4'); and each of xs and ys is 0, can be manufactured while achieving the effect of above, by employing, for example, a coupling reaction between a triphenylamine derivative having a leaving functional group such as a halogen and an amine compound, and thus, the present invention was completed.

Specifically, for manufacturing some precursors having triphenylamine structures (aniline oligomer compounds), a coupling reaction illustrated below in Reaction Formula 1 can preferably be used.

Reaction Formula 1

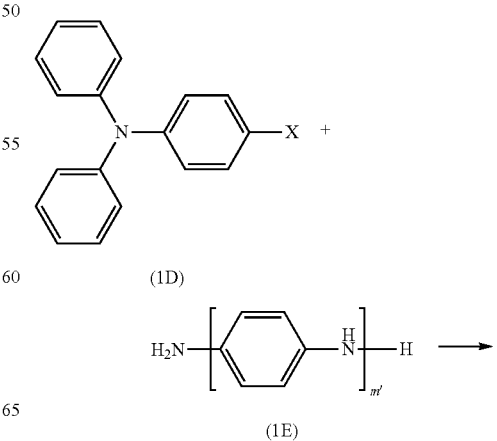

(1D)

(1E)

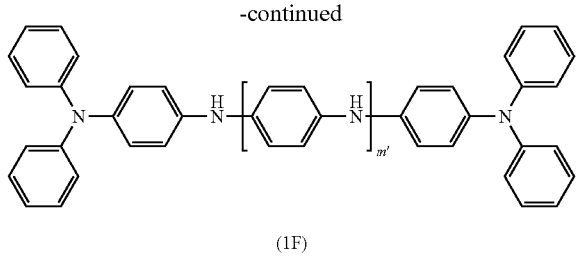

(1F)

(where X is a leaving functional group, and m' is an integer from 1 to 3).

As illustrated in Reaction Formula 1, by causing a triphenylamine derivative of Formula (1D) to react with an amine compound of Formula (1E) in a reaction solvent in the presence of a metal complex catalyst and a base, an aniline oligomer compound (an aniline compound containing a triphenylamine structure) of Formula (1F) can be manufactured.

Examples of a leaving functional group X in a triphenylamine derivative of Formula (1D) include halogen atoms and pseudohalogen groups such as sulfonic acid ester groups, and specific examples include halogen atoms, such as fluorine atom, chlorine atom, bromine atom, and iodine atom; alkylsulfonyloxy groups, such as methanesulfonyloxy group, trifluoromethanesulfonyloxy group, and nonafluorobutanesulfonyloxy group; and aromatic sulfonyloxy groups, such as benzenesulfonyloxy group and toluenesulfonyloxy group.

Among them, considering the balance between reactivity and stability of a triphenylamine derivative of Formula (1D), X is preferably a chlorine atom, a bromine atom, an iodine atom, a trifluoromethanesulfonyloxy group, or a nonafluorobutanesulfonyloxy group. In addition, considering availability of a compound of Formula (1D), X is preferably a chlorine atom, a bromine atom, or an iodine atom. Note that a compound of Formula (1D) in which X is a sulfonic acid ester group can be obtained by causing a compound of Formula (1D) in which X is hydroxy group (i.e., (diphenyl)4-hydroxyphenylamine) to react with a sulfonic acid halide or a sulfonic acid anhydride in the presence of a base.

An amine compound of Formula (1E) can preferably be used not only as a free form of an amine but also as a salt thereof, such as hydrochloride, sulfate, and acetate.

Regarding the amounts of a triphenylamine derivative of Formula (1D) and an amine compound of Formula (1E) to be used, the amount of the triphenylamine derivative of Formula (1 D) is 2 equivalents or more, preferably 2 to 3 equivalents, and particularly preferably 2 to 2.5 equivalents to the amount of the amine compound of Formula (1E).

A metal complex catalyst conventionally used in a reaction between a leaving functional group and an amino group can be used in the reaction illustrated in Reaction Formula 1, and for example, a palladium complex and a copper complex are preferably used. Such a metal complex may be a metal complex preliminarily prepared outside of the reaction system or a metal complex prepared inside of the reaction system. Also, both of them can be used in combination.

Although palladium complexes having a variety of structures can be used, what is called low-valent complexes are preferable, and zero-valent complexes having ligands of tertiary phosphines or tertiary phosphites are particularly preferable. Specific examples of tertiary phosphines or tertiary phosphites suitable as a ligand of the palladium complex include triphenylphosphine, tri-o-tolylphosphine, diphenylmethyl phosphine, phenyldimethyl phosphine, di-tert-butyl (4-dimethylaminophenyl)phosphine, 1,2-bis(diphenylphosphino)ethane, 1,3-bis(diphenylphosphino)propane, 1,4-bis(diphenylphosphino)butane, 1,1'-bis(diphenylphosphino)ferrocene, trimethylphosphine, triethylphosphine, tributylphosphine, tri-tert-butylphosphine, trimethyl phosphite, triethyl phosphite, and triphenyl phosphite. A palladium complex containing two or more types of these ligands can also be preferably used. Among these ligands, tertiary aryl phosphines, such as triphenylphosphine is preferable.

Examples of a palladium complex containing a tertiary phosphine or a tertiary phosphite as a ligand include dimethylbis(triphenylphosphine)palladium, dimethylbis(diphenylmethyl phosphine)palladium, (ethylene)bis(triphenylphosphine)palladium, bis(di-tert-butyl(4-dimethylaminophenyl) phosphine)dichloro palladium, tetrakis(triphenylphosphine) palladium, and bis(triphenylphosphine)dichloro palladium, but not limited thereto.

A suitable precursor that can be easily converted to a zero-valent complex in a reaction system can also be used as the palladium complex. Also, a low-valent complex having a ligand of a tertiary phosphine or a tertiary phosphite, which is generated in a reaction system by mixing a complex not having, as a ligand, a tertiary phosphine or a tertiary phosphite, with a tertiary phosphine or a tertiary phosphite as a ligand component, can be used as a metal complex catalyst.

Examples of the palladium complex not having a tertiary phosphine or a tertiary phosphite include bis(benzylidene acetone)palladium, tris(benzylidene acetone)dipalladium, bis(acetonitrile)dichloro palladium, bis(benzonitrile) dichloro palladium, palladium acetate, palladium chloride, and palladium-activated carbon, but not limited thereto.

In the reaction of above, a palladium complex containing a tertiary aryl phosphine as a ligand, or a palladium complex containing a tertiary alkyl phosphine as a ligand is preferably used, and a palladium complex containing triphenylphosphine or tri-tert-butylphosphine as a ligand is preferably used.

In the reaction of above, adding tetrakis(triphenylphosphine)palladium in the system to use it as a catalyst, or mixing bis(benzylidene acetone)palladium or palladium acetate and tri-tert-butylphosphine to generate a palladium complex having tri-tert-butylphosphine as a ligand, and use it as a catalyst, are particularly preferable.

Although copper complexes having a variety of structures can be used, in particular, monovalent copper complexes, such as a copper(I) chloride complex, a copper(I) bromide complex, a copper(I) iodide complex, and a copper(I) acetate complex are preferable. Examples of the ligands of these copper complexes particularly include amino acid compounds, such as proline, piperidyl carboxylic acid, and pyrrole carboxylic acid; and diamines, such as ethylenediamine, N-methylethylenediamine, N,N'-dimethyl ethylenediamine, N,N,N',N'-tetraethylenediamine, propanediamine, N,N'-dimethylpropanediamine, N,N,N',N'-tetrapropanediamine, and 1,2-diaminocyclohexane.

When such a copper complex is used as a metal complex catalyst, an iodide such as tetra-n-butyl ammonium iodide, sodium iodide, and potassium iodide can be added to efficiently facilitate a reaction. In this case, an adding amount of the iodide is preferably from 0.05 to 3 equivalents to the amount of a triphenylamine derivative (1D).

An amount of the metal complex catalyst, such as a palladium complex and a copper complex, to be used can be an amount conventionally used for catalysts, and generally, the amount is 20% by mol or less to an amine compound of Formula (1E), and usually even 10% by mol or less is sufficient to work.

When a ligand is used at the same time, an amount of the ligand is from 0.1 to 5 equivalents and preferably from 0.5 to 3 equivalents to the amount of a metal complex to be used.

In the reaction illustrated in Reaction Formula 1, the base serves as a neutralizer or a scavenger of a compound HX (X refers to the leaving functional group described above) generated during a coupling reaction.

Preferable examples of the base to be used include inorganic bases, such as sodium bicarbonate, potassium bicarbonate, potassium phosphate, sodium carbonate, potassium carbonate, lithium carbonate, cesium carbonate, sodium phosphate, and potassium phosphate; amines, such as trimethylamine, triethylamine, tripropylamine, triisopropylamine, tributylamine, diisopropylethylamine, pyridine, quinoline, and collidine; and bases such as sodium hydride, potassium hydride, tert-butoxysodium, tert-pentoxysodium, tert-butoxypotassium, and tert-pentoxypotassium. When considering reactivity and ease of handling, tert-butoxysodium, tert-pentoxysodium, tert-butoxypotassium, and tert-pentoxypotassium are preferably used.

An amount of the base to be used is from 1 to 10 equivalents and preferably from 2 to 6 equivalents to the amount of an amine compound of Formula (1E). Particularly when an amine compound of Formula (1E) is a free form, an amount of the base to be used is preferably from 2 to 4 equivalents to the amount of the amine compound. If the amount of the base to be used is less than 1 equivalent, the coupling reaction does not proceed, and thus the target product cannot be obtained.

As a reaction solvent used in the reaction illustrated in Reaction Formula 1, any solvents can be used as long as they do not react with each of the raw materials, and examples of the reaction solvent that can be used include aprotic polar organic solvents (N,N-dimethylformamide (DMF), dimethyl sulfoxide (DMSO), N,N-dimethylacetamide (DMAc), N-methyl-2-pyrrolidone (NMP), and the like), alcohols (methanol, ethanol, propanol, butanol, i-propanol, i-butanol, tert-butanol, cyclohexanol, and the like), ethers (diethyl ether ($Et_2O$), isopropyl ether (i-$PR_2O$), tert-butylmethyl ether (TBME), cyclopentylmethyl ether (CPME), tetrahydrofuran (THF), dioxane, and the like), aliphatic hydrocarbons (pentane, hexane, heptane, petroleum ether, and the like), aromatic hydrocarbons (benzene, toluene, xylene, mesitylene, chlorobenzene, dichlorobenzene, nitrobenzene, tetralin, and the like), halogen hydrocarbons (chloroform, dichloromethane, carbon tetrachloride, dichloroethane, and the like), lower fatty acid esters (methyl acetate, ethyl acetate, butyl acetate, methyl propionate, and the like), and nitriles (acetonitrile, propionitrile, butyronitrile, and the like). These solvents can be optionally selected considering the degree of ease with which the coupling reaction proceeds and the like. These solvents can be used alone, or two or more types of them can be used as a mixture. Occasionally, these solvents can also be used after being dehydrated solvents by using a suitable dehydrating agent and/or a desiccating agent.

In this manufacturing method, order of addition of the raw materials (a triphenylamine derivative of Formula (1D) and an amine compound of Formula (1E)), the metal complex catalyst, the base, and the solvent into the reaction system, and order of preparation of the metal complex catalyst in the reaction system are optionally selected considering stability of the metal complex catalyst, the solvent and the base to be used, and reactivity between the raw materials and the metal complex catalyst and the like.

The reaction of above can be conducted at a temperature within a range from −100° C. to the boiling point of a solvent to be used, preferably at a temperature within a range from −50° C. to 200° C. The reaction is conducted particularly preferably at a temperature within a range from 10° C. to 150° C., in order to cause the reaction to proceed efficiently.

Although a reaction time of the reaction is not particularly limited, it is optionally selected, for example, from 0.1 hour to 1,000 hours.

After the reaction is completed, the obtained target product may be purified by using a procedure, such as recrystallization, distillation, and silica gel column chromatography.

A manufacturing method of the present invention does not require raw materials and reagents that are difficult to obtain or expensive, and can be conducted with one step of the coupling reaction between a triphenylamine derivative and an amine compound to manufacture an aniline oligomer compound of Formula (1F) (an aniline compound containing a triphenylamine structure). Moreover, the reaction efficiently proceeds in a manufacturing method of the present invention, even if a by-product generated during the reaction, such as alcohol is not removed, and thus a target compound can be manufactured in a short time at a high yield.

EXAMPLES

The present invention will be explained in further detail according to Synthesis Examples and Examples; however, the present invention is not limited to the descriptions below.

A weight average molecular weight described in each of Synthesis Example 1 to Synthesis Example 4 below was measured by gel permeation chromatography (hereinafter, abbreviated as GPC). The GPC device manufactured by Tosoh Corporation was used for measurements, and measuring conditions are as described below. A degree of distribution shown in each of Synthesis Examples below is calculated from a weight average molecular weight and a number average molecular weight measured.

GPC column: Shodex [registered trademark] (Asahipak [registered trademark] (Showa Denko K.K.)
Column temperature: 40° C.
Solvent: N,N-dimethylformamide (DMF)
Flux: 0.6 ml/minute
Standard sample: polystyrene (Tosoh Corporation)
Detector: RI detector (Tosoh Corporation, RI-8020)

Synthesis Example 1

1.00 g of N-(4-aminophenyl)-1,4-phenylenediamine (also called N-(4-aminophenyl)-1,4-benzenediamine or 4,4'-diaminodiphenylamine) (Tokyo Chemical Industry Co., Ltd.), 3.42 g of 4-bromotriphenylamine (Tokyo Chemical Industry Co., Ltd.), 1.01 g of sodium tert-butoxide (also called tert-butoxysodium) (Tokyo Chemical Industry Co., Ltd.), and 0.04 g of bis(di-tert-butyl(4-dimethylaminophenyl)phosphine)dichloropalladium(II) (Sigma-Aldrich Corporation) were added to 25.0 g of o-xylene (Wako Pure Chemical Industries, Ltd.), and dissolved therein. The air in the reaction vessel was replaced with nitrogen gas, and the content was reacted at 135° C. for 22 hours. After the reaction was completed, the reaction solution was suction filtrated, concentrated, diluted with ethyl acetate, and extracted with a saturated saline solution. Then, an organic phase was concentrated, and recrystallized with dioxane to collect a compound. The mass of the collected compound (aniline oligomer A) was 1.46 g. A GPC analysis of the obtained aniline oligomer A showed that the weight average molecular weight was 840 in terms of standard polystyrene, and the degree of distribution was 1.01.

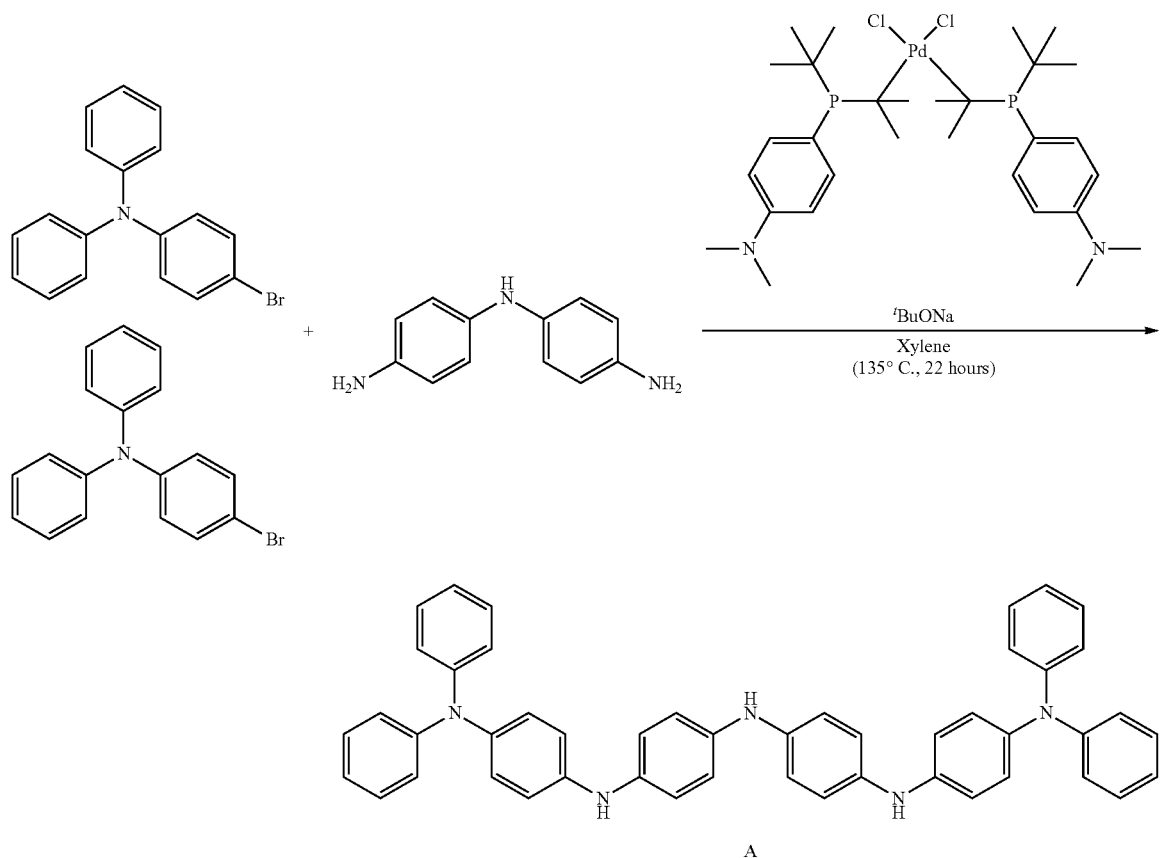

Synthesis Example 2

2.37 g of 4-aminodiphenylamine (Tokyo Chemical Industry Co., Ltd.), 2.00 g of tris(4-bromotriphenyl)amine (Tokyo Chemical Industry Co., Ltd.), 1.24 g of sodium tert-butoxide (Tokyo Chemical Industry Co., Ltd.), and 0.04 g of bis(di-tert-butyl(4-dimethylaminophenyl)phosphine)dichloropalladium (II) (Sigma-Aldrich Corporation) were added to 50.0 g of o-xylene (Wako Pure Chemical Industries, Ltd.), and dissolved therein. The air in the reaction vessel was replaced with nitrogen gas, and the content was reacted at 135° C. for 22 hours. After the reaction was completed, the reaction solution was suction filtrated, and extracted with a saturated saline solution. Then, an organic phase was concentrated, dissolved in chloroform, and reprecipitated with hexane to collect a compound. The mass of the collected compound (aniline oligomer B) was 2.56 g. A GPC analysis of the obtained aniline oligomer B showed that the weight average molecular weight was 1440 in terms of standard polystyrene, and the degree of distribution was 1.16.

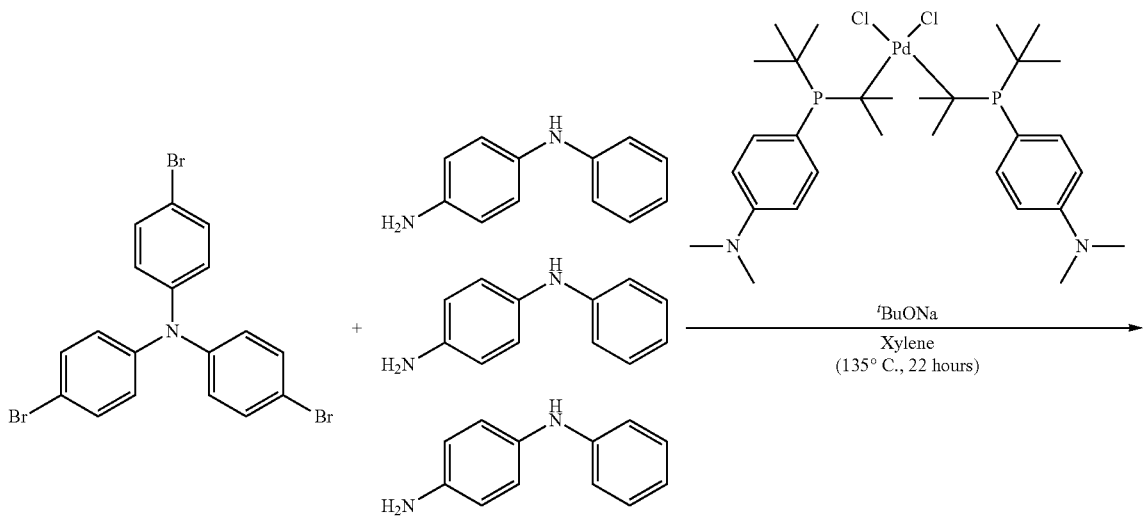

-continued

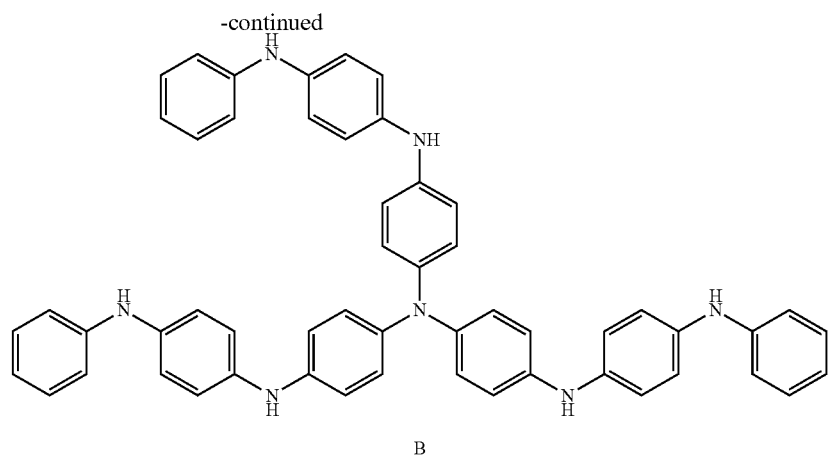

B

Synthesis Example 3

0.50 g of the aniline oligomer A obtained in Synthesis Example 1 and chlorosulfonic acid (Kanto Chemical Co., Inc.) that were 0.5 times, 0.75 times, 1 time, or 1.5 times in a molar ratio to the aromatic rings of the aniline oligomer were reacted in 25.0 g of tetrachloroethane (Tokyo Chemical Industry Co., Ltd.), at 85° C. for 5 hours. After the reaction was completed, the reaction solution was suction filtrated, washed with chloroform, and air-dried. Then, the dried product was dissolved in water, and acetone was added thereto to deposit and collect a sulfonated aniline oligomer SA. A GPC analysis showed that the sulfonated aniline oligomer SA, which was obtained by using chlorosulfonic acid that was 0.75 times in a molar ratio to the aromatic rings of the aniline oligomer A, had the weight average molecular weight of 1060 in terms of standard polystyrene and the degree of distribution of 1.15. This sulfonated aniline oligomer SA includes an oligomer compound of Formula (1A), in which each of $R_2$ and $R_3$ is a group of Formula (4), $R_1$ is a hydrogen atom, at least one of a plurality of Rs is a sulfo group, and each of a and b is 1. The sulfonated aniline oligomer SA further includes an oligomer compound (oxidized form) of Formula (1B), in which each of $R_2$ and $R_3$ is a group of Formula (4), at least one of a plurality of Rs is a sulfo group, and each of a and b is 1. Although the sulfonated aniline oligomer SA obtained in this Synthesis Example was water soluble, the aniline oligomer A obtained in Synthesis Example 1 was not water soluble, which suggests that the sulfonated aniline oligomer SA has a sulfo group. The number of the sulfo groups and the positions of substitution of the sulfo groups were hard to be identified.

Synthesis Example 4

0.50 g of the aniline oligomer B obtained in Synthesis Example 2 and chlorosulfonic acid (Kanto Chemical Co., Inc.) that were 0.75 times or 1 time in a molar ratio an aromatic ring of the aniline oligomer were reacted in 25.0 g of tetrachloroethane (Tokyo Chemical Industry Co., Ltd.), at 85° C. for 5 hours. After the reaction was completed, the reaction solution was suction filtrated, washed with chloroform, and air-dried. Then, the dried product was dissolved in water, and acetone was added thereto to deposit and collect a sulfonated aniline oligomer SB. A GPC analysis showed that the sulfonated aniline oligomer SB, which was obtained by using chlorosulfonic acid that was 1 time in a molar ratio an aromatic ring of the aniline oligomer, had the weight average molecular weight of 2170 in terms of standard polystyrene and the degree of distribution of 1.50. This sulfonated aniline oligomer SB includes an oligomer compound of Formula (1A), in which each of $R_2$ and $R_3$ is a group of Formula (3), $R_1$ is a group of Formula (2), at least one of a plurality of Rs is a sulfo group, and each of a and b is 1. Similarly to Synthesis Example 3, the sulfonated aniline oligomer SB is supposed to further include an oligomer compound that is an oxidant. Although the sulfonated aniline oligomer SB obtained in this Synthesis Example was water soluble, the aniline oligomer B obtained in Synthesis Example 2 was not water soluble, which suggests that the sulfonated aniline oligomer SB has a sulfo group. The number of the sulfo groups and the positions of substitution were hard to be identified.

Example 1

0.200 g of each of four types of the sulfonated aniline oligomers SA obtained in Synthesis Example 3 was dissolved in 9.8 g of ultrapure water containing 0.1% by mass of a surfactant (Olfine [registered trademark] EXP. 4200, Nissin Chemical Industry Co., Ltd.) to obtain a solution. Then, 10% by mass of a tetramethylammonium hydroxide aqueous solution was dropped to the solution to adjust the pH to neutral, and the solution was filtered through a polyethersulfone microfilter having the pore size of 0.2 μm to prepare a composition (solution) for forming an antistatic film.

Example 2

0.200 g of each of two types of the sulfonated aniline oligomers SB obtained in Synthesis Example 4 was dissolved in 9.8 g of ultrapure water containing 0.1% by mass of a surfactant (Olfine [registered trademark] EXP. 4200, Nissin Chemical Industry Co., Ltd.) to obtain a solution. Then, 10% by mass of a tetramethylammonium hydroxide aqueous solution was dropped to the solution to adjust the pH to neutral, and the solution was filtered through a polyethylene microfilter having the pore size of 0.2 μm to prepare a composition (solution) for forming an antistatic film.

Comparative Example 1

0.100 g of a water soluble polymer, polyvinylpyrrolidone (K-90, NIPPON SHOKUBAI CO., LTD.), was dissolved in 9.9 g of ultrapure water containing 0.1% by mass of a surfactant (Olfine [registered trademark] EXP. 4200, Nissin Chemical Industry Co., Ltd.).

<Measurement of Surface Resistance>

The antistatic property of a film closely relates to the value of surface resistance of the film. Generally known is that a lower value of surface resistance indicates a better antistatic property. Accordingly, by measuring surface resistance of a film, the antistatic property of the film can be evaluated indirectly.

A silicon wafer was spin coated with each of the solutions obtained in Example 1, Example 2, and Comparative Example 1, at 1500 rpm for 60 seconds, and was baked at 100° C. for 60 seconds to form a film. The surface resistance of the formed film was measured by using the digital insulation tester (DSM-8104, DKK-TOA CORPORATION). Table 1 shows the results. The solution obtained in Comparative Example 1 showed the highest value of surface resistance.

TABLE 1

|  | Molar Ratio of Chlorosulfonic Acid to Aromatic Ring | Surface Resistance ($\Omega$) |
|---|---|---|
| Comparative Example 1 | — | $7.4 \times 10^{13}$ |
| Example 1 | 0.5 | $7.9 \times 10^{7}$ |
|  | 0.75 | $1.9 \times 10^{7}$ |
|  | 1 | $2.0 \times 10^{9}$ |
|  | 1.5 | $8.2 \times 10^{8}$ |
| Example 2 | 0.75 | $4.8 \times 10^{8}$ |
|  | 1 | $5.6 \times 10^{8}$ |

The $^1$H-NMR device and measuring conditions thereof used in Reference Example 1, and Example 3 to Example 8 are described below.

[$^1$H-NMR]
Device: Varian NMR System 400NB (400 MHz)
Measurement Solvent: CDCl$_3$, DMSO-D$_6$
Standard Substance: tetramethylsilane (TMS) ($\delta$0.0 ppm for $^1$H), or CDCl$_3$ ($\delta$7.26 ppm for $^1$H)

Reference Example 1

According to the manufacturing method disclosed in WO 2008/129947, except that the step for protecting and deprotecting an amino group using a protecting group such as the t-butoxycarbonyl group (Boc group) is not conducted, the aniline oligomer compound A was synthesized as illustrated in the reaction formula below.

4,4'-dibromodiphenylamine (2.00 g, 6.12 mmol) and 4-aminotriphenylamine (3.34 g, 12.84 mmol) were suspended in xylene (40 g), and tetrakis (triphenylphosphine)palladium [Pd(PPh$_3$)$_4$] (0.2120 g, 0.1835 mmol) as a metal complex catalyst and tert-butoxysodium [t-BuONa] (1.234 g, 12.84 mmol) as a base were added thereto, and stirred in nitrogen atmosphere, at 130° C. for 32 hours to be reacted.

An analysis by liquid chromatography showed that an area percentage of the target compound A was only 12.3% after the reaction for 32 hours.

That is, the result of this Reference Example indicated that when the reaction is conducted without protecting nitrogen of 4,4'-dibromodiphenylamine with a protecting group such as the Boc group, the target compound may not efficiently be obtained.

Example 3

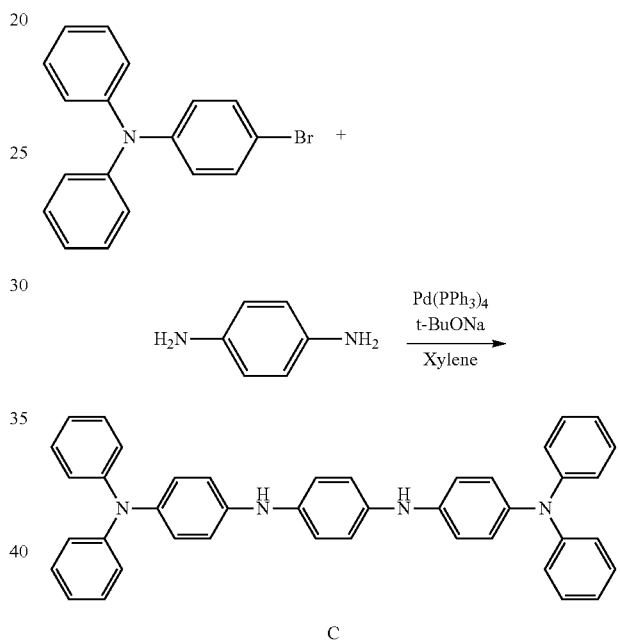

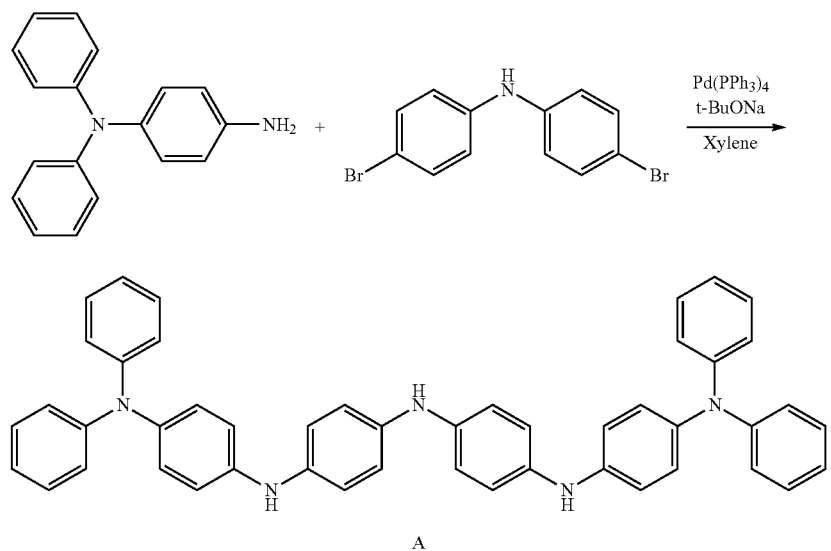

p-phenylenediamine (2.00 g, 18.49 mmol) and 4-bromotriphenylamine (12.59 g, 38.84 mmol) were suspended in xylene (40 g), and Pd(PPh$_3$)$_4$ (0.64 g, 0.55 mmol) as a metal complex catalyst and t-BuONa (3.91 g, 40.69 mmol) as a base were added thereto, and stirred in nitrogen atmosphere, at 135° C. for 10 hours to be reacted. The reaction mixture was cooled to fully deposit the product, and then filtered. To remove inorganic salts, the filtrate was stirred in water to be washed. The filtration residue was recrystallized with 1,4-dioxane to obtain the target aniline oligomer compound C (obtained amount: 7.68 g, yield: 70%).

$^1$H-NMR (DMSO-d$_6$): δ7.93 (S, 2H), 7.26-7.20 (m, 8H), 7.03 (S, 4H), 6.99-6.90 (m, 20H).

Example 4

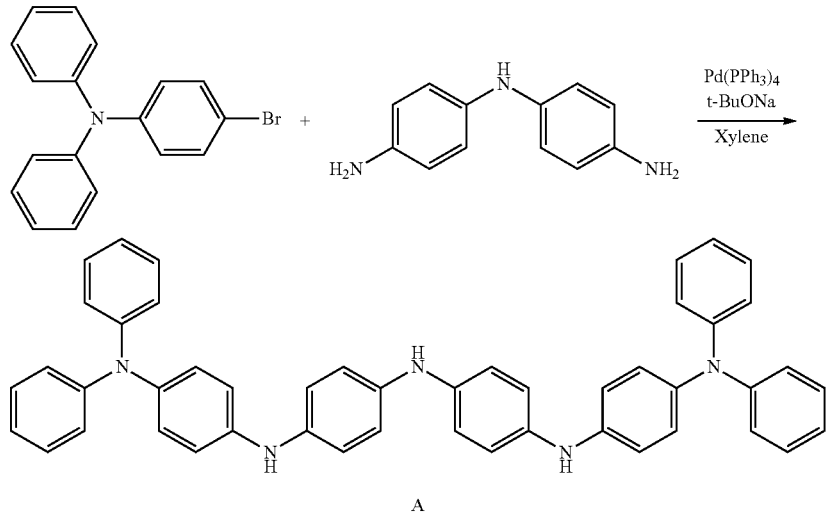

A 4,4'-diaminodiphenylamine (10.00 g, 50.19 mmol) and 4-bromotriphenylamine (34.17 g, 105.40 mmol) were suspended in xylene (100 g), and Pd(PPh$_3$)$_4$ (0.5799 g, 0.5018 mmol) as a metal complex catalyst and t-BuONa (10.13 g, 105.40 mmol) as a base were added thereto, and stirred in nitrogen atmosphere, at 130° C. for 14 hours to be reacted. At this point, an analysis by liquid chromatography showed that an area percentage of the target compound A was already 97.18%.

The reaction mixture was filtered, and a saturated saline solution was added to the filtrate to perform separating extraction. The solvent was removed from the organic phase by distillation to obtain a crude product containing the target product. Then, the target product was recrystallized from 1,4-dioxane. Thus, aniline oligomer compound A was obtained (obtained amount: 22.37 g, yield: 65%).

$^1$H-NMR (CDCl$_3$): δ7.83 (S, 2H), 7.68 (S, 1H), 7.26-7.20 (m, 8H), 7.01-6.89 (m, 28H).

Example 5

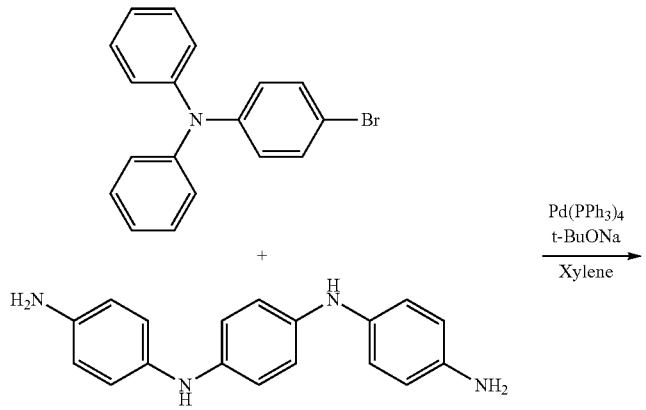

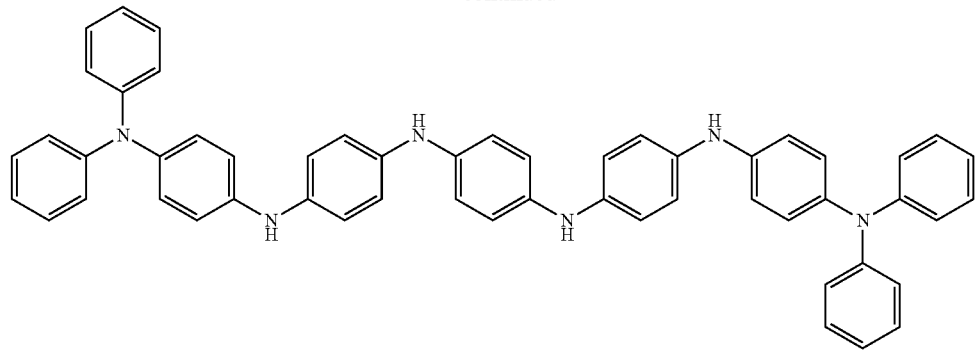

D

N,N'-bis(4-aminophenyl)-p-phenylenediamine (5.00 g, 17.22 mmol) and 4-bromotriphenylamine (9.30 g, 28.70 mmol) were suspended in xylene (140 g), and Pd(PPh₃)₄ (0.33 g, 0.29 mmol) as a metal complex catalyst and t-BuONa (2.76 g, 28.70 mmol) as a base were added thereto, and stirred in nitrogen atmosphere, at 135° C. for 8 hours to be reacted. The reaction mixture was cooled and filtered, and then the solvent was removed by distillation under reduced pressure to obtain a crude product containing the target product. Then, the target product was recrystallized from 1,4-dioxane. Thus, aniline oligomer compound D was obtained (obtained amount: 5.94 g, yield: 53%).

$^1$H-NMR (DMSO-$d_6$): δ7.81 (S, 2H), 7.61 (S, 2H), 7.27-7.18 (m, 8H), 7.05-6.65 (m, 32H).

The starting material N,N'-bis(4-aminophenyl)-p-phenylenediamine used in this reaction was prepared with p-phenylenediamine and 1,4-benzoquinone as raw materials, according to the description of WO 2008/129947.

Example 6

4,4'-diaminodiphenylamine (2.00 g, 10.04 mmol) and 4-bromotriphenylamine (6.67 g, 20.58 mmol) were suspended in toluene (20 g), and bis(benzylidene acetone)palladium [Pd(dba)₂ (0.0577 g, 0.100 mmol)] as a metal complex catalyst, ligand: tri-tert-butylphosphine [t-Bu₃P] (19.48 μL, 0.0803 mmol), and t-BuONa (2.89 g, 30.11 mmol) as a base were added thereto, and stirred in nitrogen atmosphere, at 25° C. for 3 hours to be reacted. The reaction mixture was filtered, and a saturated saline solution was added to the filtrate to perform separating extraction. The solvent was removed from the organic phase by distillation to obtain a crude product containing the target product. Then, the target product was recrystallized from 1,4-dioxane and isopropanol. Thus, aniline oligomer compound A was obtained (obtained amount: 3.92 g, yield: 57%).

Note that $^1$H-NMR of the obtained aniline oligomer compound A was identical to that obtained in Example 4.

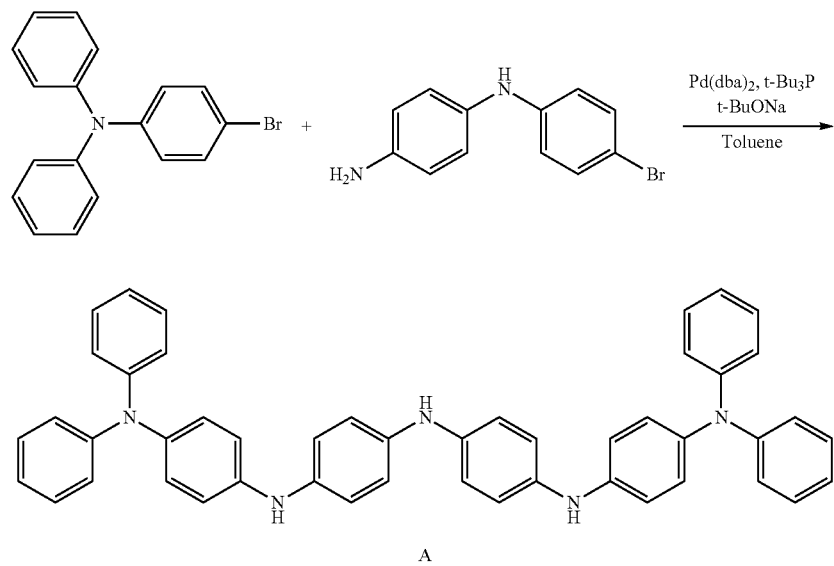

A

Example 7

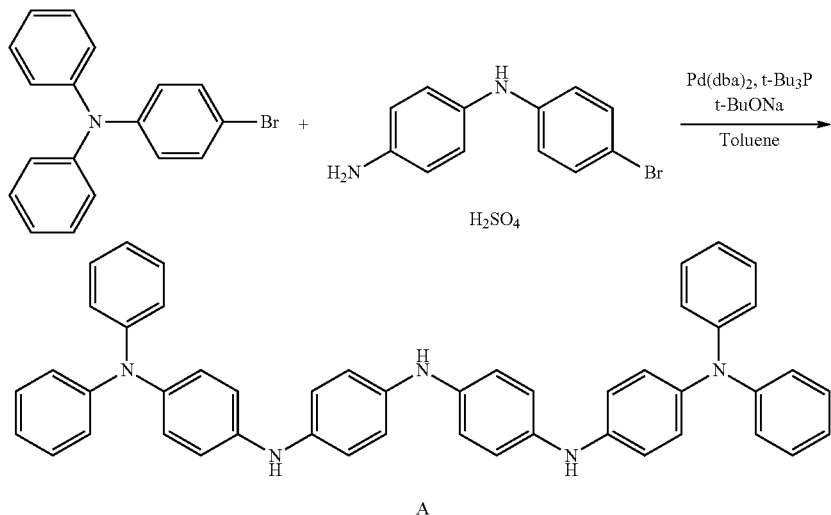

4,4'-diaminodiphenylamine sulfate (5.00 g, 16.82 mmol) and 4-bromotriphenylamine (11.45 g, 35.31 mmol) were suspended in toluene (150 g), and Pd(dba)$_2$ (0.0967 g, 0.168 mmol) as a metal complex catalyst, ligand: t-Bu$_3$P (0.359 mL, 0.135 mmol, 0.375 N (in toluene)), and t-BuONa (8.08 g, 84.08 mmol) as a base were added thereto, and stirred in nitrogen atmosphere, at 70° C. for 4 hours to be reacted. The reaction mixture was filtered, and a saturated saline solution was added to the filtrate to perform separating extraction. After the organic phase was dried over magnesium sulfate, the solvent was removed by distillation to obtain a crude product containing the target product. Then, the target product was recrystallized from 1,4-dioxane. Thus, aniline oligomer compound A was obtained (obtained amount: 7.44 g, yield: 65%).

Note that $^1$H-NMR of the obtained aniline oligomer compound A was identical to that obtained in Example 4.

Example 8

4,4'-diaminodiphenylamine sulfate (5.00 g, 16.82 mmol) and 4-bromotriphenylamine (11.45 g, 35.31 mmol) were suspended in xylene (100 g), and Pd(PPh$_3$)$_4$ (0.583 g, 0.505 mmol) as a metal complex catalyst and tert-pentoxysodium [t-AmONa] (8.33 g, 75.67 mmol) as a base were added thereto, and stirred in nitrogen atmosphere, at 130° C. for 6 hours to be reacted. The reaction mixture was filtered, and a saturated saline solution was added to the filtrate to perform separating extraction. After the organic phase was dried over magnesium sulfate, the solvent was removed by distillation to obtain a crude product containing the target product. Then, the target product was recrystallized from 1,4-dioxane. Thus, aniline oligomer compound A was obtained (obtained amount: 6.60 g, yield: 57%).

Note that $^1$H-NMR of the obtained aniline oligomer compound A was identical to that obtained in Example 4.

The invention claimed is:
1. A method for manufacturing an aniline oligomer compound of Formula (1C'):

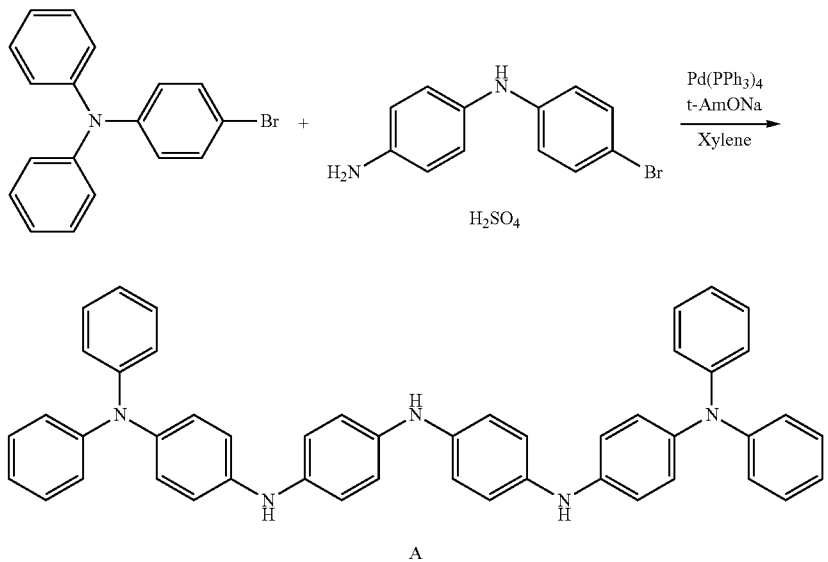

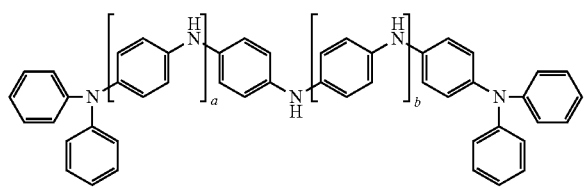

(1C′)

where a and b are positive integers satisfying 2≤(a+b)≤3, the method comprising:
causing a triphenylamine derivative of Formula (1D) to react with an amine compound of Formula (1E) in the presence of a metal complex catalyst and a base:

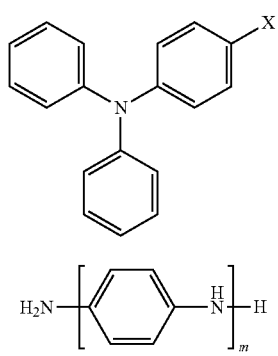

(1D)

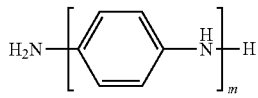

(1E)

where X is a leaving functional group, and m is 2 or 3.

2. The method for manufacturing according to claim 1 wherein
the leaving functional group is a group selected from the group consisting of a halogen atom, a methanesulfonyloxy group, a benzenesulfonyloxy group, a toluenesulfonyloxy group, a trifluoromethanesulfonyloxy group, and a nonafluorobutanesulfonyloxy group.

3. The method for manufacturing according to claim 2, wherein
the leaving functional group is selected from the group consisting of a chlorine atom, a bromine atom, and an iodine atom.

4. The method for manufacturing according to claim 1 wherein
the metal complex catalyst is a palladium complex.

5. A method for manufacturing an aniline oligomer compound of Formula (1F), the method comprising:
causing a triphenylamine derivative of Formula (1D) to react with an amine compound of Formula (1E) in the presence of a metal complex catalyst and a base:

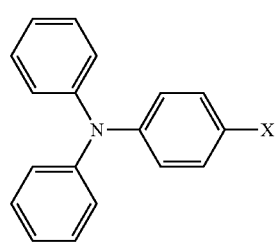

(1D)

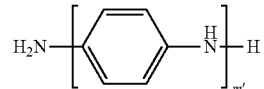

(1E)

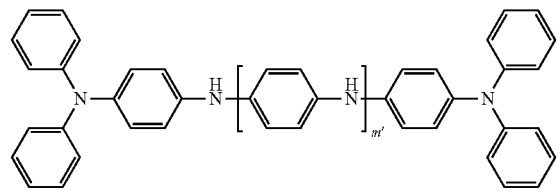

(1F)

where x is a leaving functional group, and m′ is an integer from 1 to 33.

6. The method for manufacturing according to claim 5, wherein
the leaving functional group is a group selected from the group consisting of a halogen atom, a methanesulfonyloxy group, a benzenesulfonyloxy group, a toluenesulfonyloxy group, a trifluoromethanesulfonyloxy group, and a nonafluorobutanesulfonyloxy group.

7. The method for manufacturing according to claim 6, wherein
the leaving functional group is selected from the group consisting of a chlorine atom, a bromine atom, and an iodine atom.

8. The method for manufacturing according to claim 5, wherein
the metal complex catalyst is a palladium complex.

* * * * *